(12) United States Patent
Jikuhara et al.

(10) Patent No.: US 12,322,502 B2
(45) Date of Patent: Jun. 3, 2025

(54) INFORMATION PROCESSING APPARATUS, METHOD, AND NON-TRANSITORY COMPUTER READABLE MEDIUM

(71) Applicant: TOYOTA JIDOSHA KABUSHIKI KAISHA, Toyota (JP)

(72) Inventors: Yoshikazu Jikuhara, Miyoshi (JP); Seii Sai, Yokohama (JP); Ibuki Shimada, Miyoshi (JP); Takahiro Aoki, Saitama (JP); Keishi Kinoshita, Tokyo-to (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 225 days.

(21) Appl. No.: 18/312,054

(22) Filed: May 4, 2023

(65) Prior Publication Data

US 2023/0360784 A1    Nov. 9, 2023

(30) Foreign Application Priority Data

May 6, 2022    (JP) .................................. 2022-076658

(51) Int. Cl.
*G16H 40/20*    (2018.01)
*G06Q 50/26*    (2024.01)

(52) U.S. Cl.
CPC ............. *G16H 40/20* (2018.01); *G06Q 50/26* (2013.01); *G06Q 2240/00* (2013.01)

(58) Field of Classification Search
CPC ..... G16H 40/20; G06Q 50/26; G06Q 2240/00
See application file for complete search history.

(56) References Cited

U.S. PATENT DOCUMENTS

2021/0035038 A1    2/2021    Suzuki et al.

FOREIGN PATENT DOCUMENTS

| JP | 2001124569 A | 5/2001 |
| JP | 2006059056 A | 3/2006 |
| JP | 2018173925 A | 11/2018 |
| JP | 2021022332 A | 2/2021 |
| JP | 2021086246 A | 6/2021 |

*Primary Examiner* — Michael D Lang
(74) *Attorney, Agent, or Firm* — Dickinson Wright, PLLC (57) ABSTRACT

A controller of an information processing apparatus is configured to determine a stop location for a health checkup vehicle at which travel distances required for patients of health checkups to be performed on the health checkup vehicle to travel to the health checkup vehicle are equal to or less than a predetermined threshold, calculate a parking allowable number at the stop location or a parking allowable number at a parking lot in a vicinity of the stop location, and suggest, in a case in which the patients include more patients who plan to travel using vehicles than the parking allowable number, transportation means other than the vehicles to the patients who plan to travel using the vehicles.

15 Claims, 4 Drawing Sheets

FIG. 1

INFORMATION PROCESSING APPARATUS, METHOD, AND NON-TRANSITORY COMPUTER READABLE MEDIUM

CROSS-REFERENCE TO RELATED APPLICATION

This application claims priority to Japanese Patent Application No. 2022-076658 filed on May 6, 2022, the entire contents of which are incorporated herein by reference.

TECHNICAL FIELD

The present disclosure relates to an information processing apparatus, a method, and a program.

BACKGROUND

Patent Literature (PTL) 1 discloses technology for determining health checkup equipment to be installed in a vehicle based on information on users who plan to receive health checkups.

CITATION LIST

Patent Literature

PTL 1: JP 2021-022332 A

SUMMARY

However, the technology is not necessarily convenient when a location far from homes of patients of health checkups is set as a place for performing the health checkups. Therefore, there is room for enhancement with respect to technology for improving convenience of health checkups.

It would be helpful to enhance technology for improving convenience of health checkups.

An information processing apparatus according to an embodiment of the present disclosure includes a controller configured to:
  determine a stop location for a health checkup vehicle at which travel distances required for patients of health checkups to be performed on the health checkup vehicle to travel to the health checkup vehicle are equal to or less than a predetermined threshold;
  calculate a parking allowable number at the stop location or a parking allowable number at a parking lot in the vicinity of the stop location; and
  suggest, in a case in which the patients include more patients who plan to travel using vehicles than the parking allowable number, transportation means other than the vehicles to the patients who plan to travel using the vehicles.

A method according to an embodiment of the present disclosure is a method performed by an information processing apparatus, the method including:
  determining a stop location for a health checkup vehicle at which travel distances required for patients of health checkups to be performed on the health checkup vehicle to travel to the health checkup vehicle are equal to or less than a predetermined threshold;
  calculating a parking allowable number at the stop location or a parking allowable number at a parking lot in the vicinity of the stop location; and
  suggesting, in a case in which the patients include more patients who plan to travel using vehicles than the parking allowable number, transportation means other than the vehicles to the patients who plan to travel using the vehicles.

A program according to an embodiment of the present disclosure is configured to cause a computer to execute operations, the operations including:
  determining a stop location for a health checkup vehicle at which travel distances required for patients of health checkups to be performed on the health checkup vehicle to travel to the health checkup vehicle are equal to or less than a predetermined threshold;
  calculating a parking allowable number at the stop location or a parking allowable number at a parking lot in the vicinity of the stop location; and
  suggesting, in a case in which the patients include more patients who plan to travel using vehicles than the parking allowable number, transportation means other than the vehicles to the patients who plan to travel using the vehicles.

According to an embodiment of the present disclosure, technology for improving convenience of health checkups can be enhanced.

BRIEF DESCRIPTION OF THE DRAWINGS

In the accompanying drawings.

DETAILED DESCRIPTION

Hereinafter, an embodiment of the present disclosure will be described.

Figure 1:
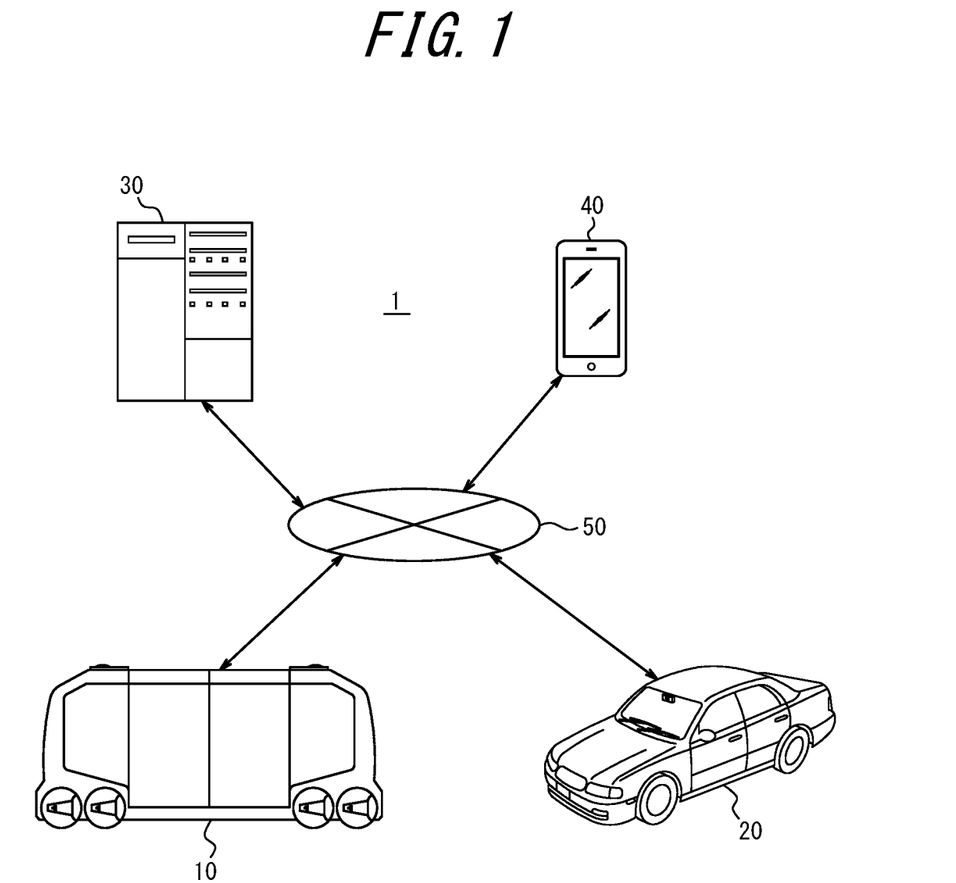
FIG. 1 is a block diagram illustrating a schematic configuration of a system according to an embodiment of the present disclosure.

An outline of a system 1 according to the embodiment of the present disclosure will be described with reference to FIG. 1.

The system 1 includes a health checkup vehicle 10, vehicles 20, an information processing apparatus 30, and terminal apparatuses 40.

The health checkup vehicle 10, the vehicles 20, the information processing apparatus 30, and the terminal apparatuses 40 are communicably connected to a network 50.

The health checkup vehicle 10 is, for example, an automobile equipped with equipment used for health checkups, but not limited to this and may be any vehicle. The automobile is, for example, a gasoline vehicle, a battery electric vehicle (BEV), a hybrid electric vehicle (HEV), a plug-in hybrid electric vehicle (PHEV), a fuel cell electric vehicle (FCEV), or the like, but is not limited to these. The health checkup vehicle 10 may be driven by a driver, or the driving may be automated at any level. The level of automation is, for example, one of level 1 to level 5 according to the classification of the Society of Automotive Engineers (SAE). The equipment used for health checkups may include, for example, a blood pressure monitor, blood testing equipment, an electrocardiograph, X-ray imaging equipment, ultrasound equipment, computed tomography (CT) equipment, or magnetic resonance imaging (MRI) equipment, but is not limited to these.

Each of the vehicles 20 is an automobile, for example, but is not limited to this and may be any vehicle. The automobile is, for example, a gasoline automobile, a BEV, an HEV, a PHEV, an FCEV, or the like, but is not limited to these. The vehicles 20 may each be driven by a driver, or the driving may be automated at any level. The level of automation is, for example, one of level 1 to level 5 according to the classification of the Society of Automotive Engineers (SAE). The vehicles 20 may be dedicated Mobility as a Service (MaaS) vehicles.

The information processing apparatus 30 is a computer such as a server that belongs to a cloud computing system or another type of computing system.

Each of the terminal apparatuses 40 is a mobile device such as a mobile phone, a smartphone, or a tablet.

The network 50 includes the Internet, at least one wide area network (WAN), at least one metropolitan area network (MAN), or any combination thereof. The network 50 may include at least one wireless network, at least one optical network, or any combination thereof. The wireless network is, for example, an ad hoc network, a cellular network, a wireless local area network (LAN), a satellite communication network, or a terrestrial microwave network.

An outline of the present embodiment will be described with reference to FIG. 1.

A controller 31 of the information processing apparatus 30 determines a stop location for the health checkup vehicle 10 at which travel distances required for patients of health checkups to be performed on the health checkup vehicle 10 to travel to the health checkup vehicle 10 are equal to or less than a predetermined threshold. The controller 31 of the information processing apparatus 30 then calculates a parking allowable number at the stop location or a parking allowable number at a parking lot in the vicinity of the stop location. Then, in a case in which the patients include more patients who plan to travel using the vehicles 20 than the parking allowable number, the controller 31 of the information processing apparatus 30 suggests transportation means other than the vehicles 20 to the patients who plan to travel using the vehicles 20.

According to the present embodiment, the location for performing the health checkups, accompanied by a parking lot, is set close to homes of the patients of the health checkups. Thus, technology for improving convenience of health checkups can be enhanced.

Figure 2:
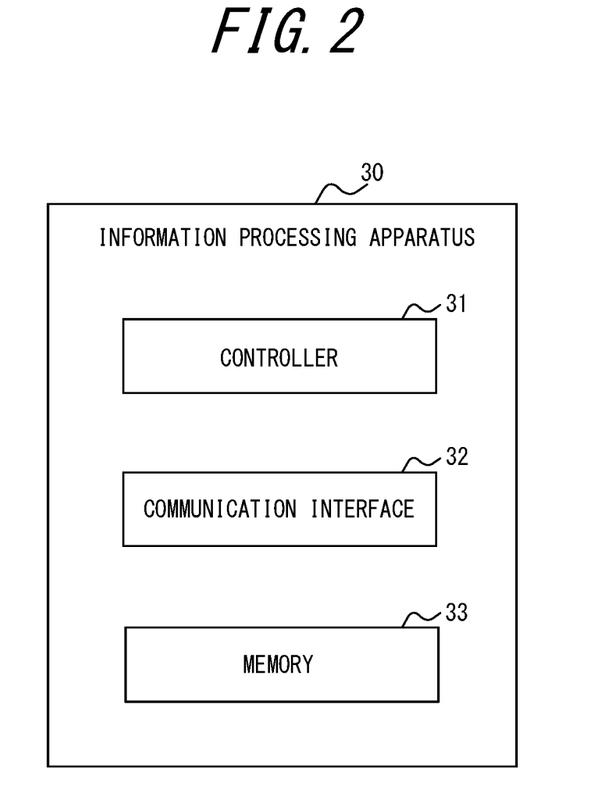
FIG. 2 is a block diagram illustrating a schematic configuration of an information processing apparatus according to the embodiment of the present disclosure.

A configuration of the information processing apparatus 30 according to the present embodiment will be described with reference to FIG. 2.

The information processing apparatus 30 includes the controller 31, a communication interface 32, and a memory 33.

The controller 31 includes at least one processor, at least one programmable circuit, at least one dedicated circuit, or any combination thereof. The processor is a general purpose processor such as a central processing unit (CPU) or a graphics processing unit (GPU), or a dedicated processor that is dedicated to specific processing. The programmable circuit is, for example, a field-programmable gate array (FPGA). The dedicated circuit is, for example, an application specific integrated circuit (ASIC). The controller 31 executes processes related to the operations of the information processing apparatus 30 while controlling the components of the information processing apparatus 30.

The communication interface 32 includes at least one interface for communication. The interface for communication is compliant with, for example, a mobile communication standard, a wired LAN standard, or a wireless LAN standard, but not limited to these, and may be compliant with any communication standard. The communication interface 32 receives data to be used for the operations of the information processing apparatus 30, and transmits data obtained by the operations of the information processing apparatus 30.

The memory 33 includes at least one semiconductor memory, at least one magnetic memory, at least one optical memory, or any combination thereof. The semiconductor memory is, for example, random access memory (RAM) or read only memory (ROM). The RAM is, for example, static random access memory (SRAM) or dynamic random access memory (DRAM). The ROM is, for example, electrically erasable programmable read only memory (EEPROM). The memory 33 functions as, for example, a main memory, an auxiliary memory, or a cache memory. The memory 33 stores data to be used for the operations of the information processing apparatus 30 and data obtained by the operations of the information processing apparatus 30. In the present embodiment, the data to be used for the operations of the information processing apparatus 30 includes a system program, an application program, a database, map information, and the like.

Figure 3:
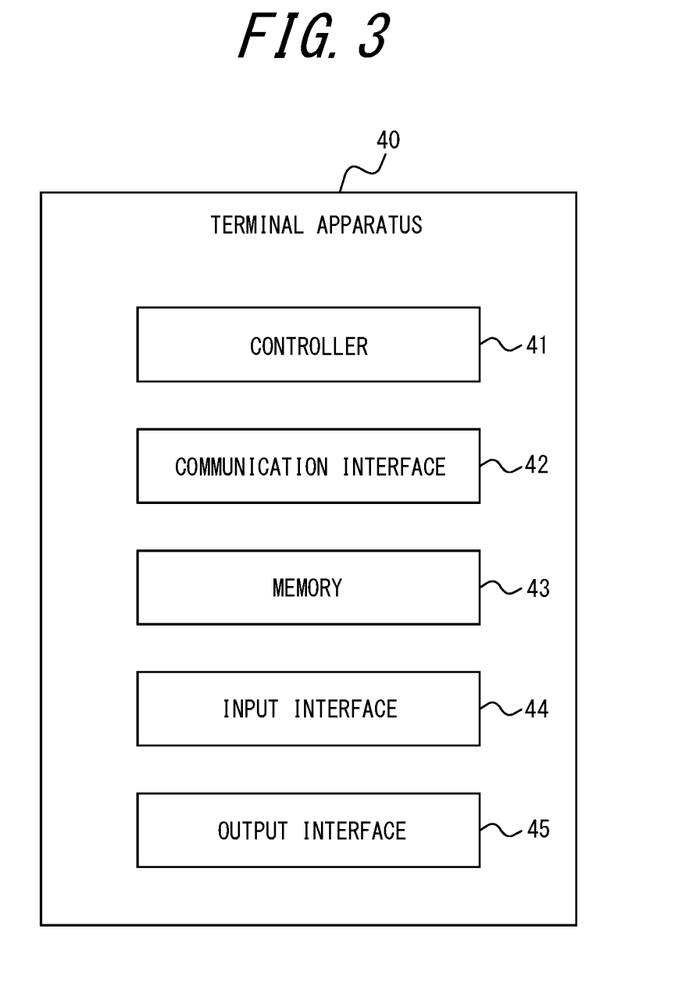
FIG. 3 is a block diagram illustrating a schematic configuration of a terminal apparatus according to the embodiment of the present disclosure.

A configuration of each terminal apparatus 40 according to the present embodiment will be described with reference to FIG. 3.

Each terminal apparatus 40 includes a controller 41, a communication interface 42, a memory 43, an input interface 44, and an output interface 45.

The controller 41 includes at least one processor, at least one programmable circuit, at least one dedicated circuit, or any combination thereof. The processor is a general purpose processor such as a CPU or a GPU, or a dedicated processor that is dedicated to specific processing. The programmable circuit is, for example, an FPGA. The dedicated circuit is, for example, an ASIC. The controller 41 executes processes related to operations of the terminal apparatus 40 while controlling the components of the terminal apparatus 40.

The communication interface 42 includes at least one interface for communication. The interface for communication is, for example, an interface compliant with a mobile communication standard such as a Long Term Evolution (LTE), the 4th generation (4G) standard, or the 5th generation (5G) standard, an interface compliant with a short-range wireless communication standard such as Bluetooth® (Bluetooth is a registered trademark in Japan, other countries, or both), or a LAN interface. The communication interface 42 receives data to be used for the operations of the terminal apparatus 40, and transmits data obtained by the operations of the terminal apparatus 40.

The memory 43 includes at least one semiconductor memory, at least one magnetic memory, at least one optical memory, or any combination thereof. The semiconductor memory is, for example, RAM or ROM. The RAM is, for example, SRAM or DRAM. The ROM is, for example, EEPROM. The memory 43 functions as, for example, a main memory, an auxiliary memory, or a cache memory. The memory 43 stores data to be used for the operations of the terminal apparatus 40 and data obtained by the operations of the terminal apparatus 40.

The input interface 44 includes at least one interface for input. The interface for input is, for example, a physical key, a capacitive key, a pointing device, a touch screen integrally provided with a display, a camera, a light detection and ranging or laser imaging, detection, and ranging (LiDAR) sensor, or a microphone. The input interface 44 accepts an operation for inputting data to be used for the operations of the terminal apparatus 40. The input interface 44 may be connected to the terminal apparatus 40 as an external input device, instead of being included in the terminal apparatus 40. As an interface for connection, for example, an interface compliant with a standard such as Universal Serial Bus (USB), HDMI® (HDMI is a registered trademark in Japan, other countries, or both), or Bluetooth® can be used.

The output interface 45 includes at least one interface for output. The interface for output is, for example, a display or a speaker. The display is, for example, a liquid crystal display (LCD) or an organic electro luminescent (EL) display. The output interface 45 outputs data obtained by the operations of the terminal apparatus 40. The output interface 45 may be connected to the terminal apparatus 40 as an external output device, instead of being included in the terminal apparatus 40. As an interface for connection, for example, an interface compliant with a standard such as USB, HDMI®, or Bluetooth® can be used.

Figure 4:
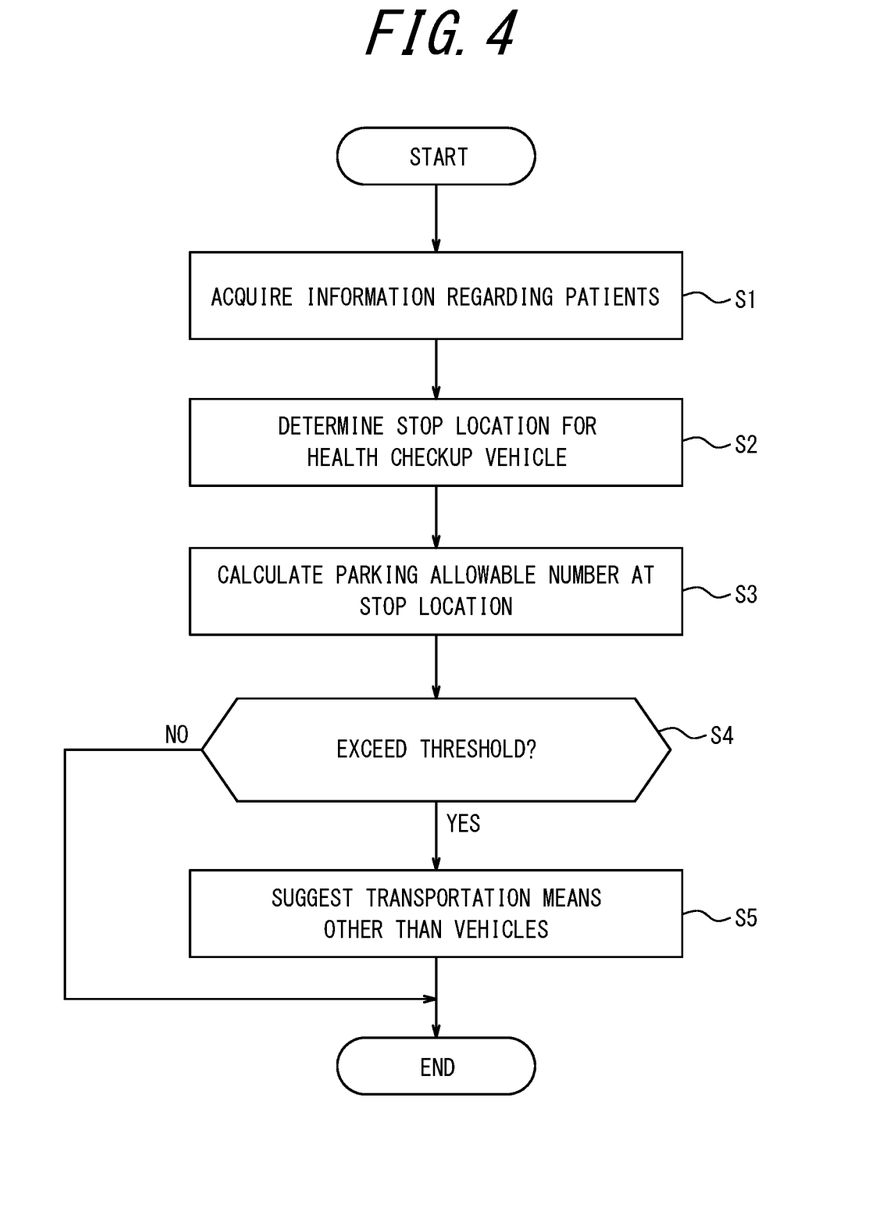
FIG. 4 is a flowchart illustrating operations of the information processing apparatus according to the embodiment of the present disclosure.

Operations of the information processing apparatus 30 according to the present embodiment will be described with reference to FIG. 4. These operations correspond to a method according to an embodiment of the present disclosure.

Step S1: The controller 31 of the information processing apparatus 30 acquires information regarding patients of health checkups to be performed on the health checkup vehicle 10.

Specifically, the controller 41 of each terminal apparatus 40 controls the input interface 44 to accept an operation by a patient of a health checkup to be performed on the health checkup vehicle 10 (a person scheduled to receive the health checkup) to input information regarding the patient, including location information on a home of the patient, on an application running on the terminal apparatus 40 for making an appointment for the health checkup via the Internet. The information regarding the patient may include, in addition to the location information on the home of the patient, information indicating a transportation means (walking, vehicle, train, bus, or the like) for the patient to a location for performing the health checkup (temporary parking space for the health checkup vehicle 10). The controller 41 of each terminal apparatus 40 then controls the communication interface 42 to transmit the information regarding the patient to the information processing apparatus 30. The controller 31 of the information processing apparatus 30 controls the communication interface 32 to receive the information regarding the patient from each terminal apparatus 40.

Step S2: The controller 31 of the information processing apparatus 30 determines, based on the information regarding the patients acquired in step S1, a stop location for the health checkup vehicle 10 at which travel distances required for the patients to travel to the health checkup vehicle 10 are equal to or less than a predetermined threshold.

Specifically, assuming that location information on multiple candidate locations for performing the health checkups (candidate stop locations for the health checkup vehicle 10) is stored in advance in the memory 33 of the information processing apparatus 30. Based on the location information on homes of the patients acquired in step S1 and the location information on the multiple candidate locations stored in the memory 33, the controller 31 of the information processing apparatus 30 identifies a location at which travel distances required for the patients to travel to the health checkup vehicle 10 are equal to or less than a predetermined threshold, from among the multiple candidate locations. The predetermined threshold may be, for example, 1 to 2 km, which corresponds to a walkable distance, but is not limited to this and can be arbitrarily determined. The controller 31 of the information processing apparatus 30 then determines the identified location as a stop location for the health checkup vehicle 10.

When the multiple patients are present, the controller 31 of the information processing apparatus 30 may determine, using any optimization algorithm, a location at which the sum of travel distances of all the patients is minimized from among the multiple candidate locations, as a stop location for the health checkup vehicle 10, based on the location information on the home of each patient and the location information on the multiple candidate locations.

Step S3: The controller 31 of the information processing apparatus 30 calculates a parking allowable number at the stop location determined in step S2.

Specifically, the controller 31 of the information processing apparatus 30 calculates a parking allowable number at the stop location determined in step S2, based on location information on the stop location determined in step S2 and map information stored in the memory 33. For example, the controller 31 of the information processing apparatus 30 may calculate a parking allowable number for the vehicles 20 other than the health checkup vehicle 10 at the stop location determined in step S2, by comparing the size of the stop location determined in step S2 with the size of a parking space specified by the Ministry of Land, Infrastructure, Transport and Tourism. Additionally or alternatively, the controller 31 of the information processing apparatus 30 may calculate a parking allowable number based on specifications of the vehicles 20 owned by the patients, which are acquired in any method on the application running on each terminal apparatus 40 for making an appointment for the health checkup via the Internet, for example. The specifications may include a vehicle type such as a mini-vehicle, small passenger vehicle, standard passenger vehicle, small freight vehicle, or large freight vehicle, but is not limited to this.

Additionally or alternatively, the controller 31 of the information processing apparatus 30 may calculate a parking allowable number at one or more parking lots located in the vicinity (for example, within 5-minute walking) of the stop location determined in step S2. A calculation method is the same as described above.

Step S4: The controller 31 of the information processing apparatus 30 determines whether the patients include more patients who plan to travel using the vehicles 20 than the parking allowable number calculated in step S3. When the number of patients who plan to travel using the vehicles 20 exceeds the parking allowable number calculated in step S3, the process proceeds to step S5. On the other hand, when the number of patients who plan to travel using the vehicles 20 does not exceed the parking allowable number calculated in step S3, the process ends, for example, with a reservation completion notice being presented to the patients in any method.

Step S5: the controller 31 of the information processing apparatus 30 suggests transportation means other than the vehicles 20 to the patients who plan to travel using the vehicles 20.

Specifically, the controller 31 of the information processing apparatus 30 identifies the terminal apparatuses 40 of the patients who plan to travel using the vehicles 20, based on the information regarding the patients acquired in step S1.

The controller 31 of the information processing apparatus 30 then generates messages suggesting transportation means other than the vehicles 20. The controller 31 of the information processing apparatus 30 controls the communication interface 32 to transmit the generated messages to the identified terminal apparatuses 40. The controller 41 of each terminal apparatus 40 then controls the output interface 45 to output the message received from the information processing apparatus 30 by screen display or audio to each of the patients who plan to travel using the vehicles 20. The messages may be any message that suggests walking or using public transportation such as buses or trains, as the transportation means other than the vehicles 20, but are not limited to this.

Additionally or alternatively, the controller 31 of the information processing apparatus 30 may further identify one or more patients to whom the transportation means other than the vehicles 20 are to be suggested, from among the patients who plan to travel using the vehicles 20, based on the location information on the homes of the patients. Specifically, the controller 31 of the information processing apparatus 30 further identifies one or more patients whose distances from train stations, bus stops, or the like to homes are equal to or less than a predetermined threshold (for example, within 5-minute walking), from among the patients who plan to travel using the vehicles 20, based on the location information on the homes of the patients and the map information stored in the memory 33. The controller 31 of the information processing apparatus 30 then suggests the transportation means other than the vehicles 20 to the further identified patients in the same manner as described above.

As described above, the controller 31 of the information processing apparatus 30 according to the present embodiment determines a stop location for the health checkup vehicle 10 at which travel distances required for patients of health checkups to be performed on the health checkup vehicle 10 to travel to the health checkup vehicle 10 are equal to or less than a predetermined threshold. The controller 31 of the information processing apparatus 30 then calculates a parking allowable number at the stop location. Then, in a case in which the patients include more patients who plan to travel using the vehicles 20 than the parking allowable number, the controller 31 of the information processing apparatus 30 suggests transportation means other than the vehicles 20 to the patients who plan to travel using the vehicles 20.

According to such a configuration, for example, the location for performing the health checkups, accompanied by a parking lot, can be set close to homes of the patients of the health checkups. Thus, technology for improving convenience of health checkups can be enhanced.

While the present disclosure has been described with reference to the drawings and examples, it should be noted that various modifications and revisions may be implemented by those skilled in the art based on the present disclosure. Accordingly, such modifications and revisions are included within the scope of the present disclosure. For example, functions or the like included in each component, each step, or the like can be rearranged without logical inconsistency, and a plurality of components, steps, or the like can be combined into one or divided.

As a variation, an embodiment in which the configuration and operations of the information processing apparatus 30 are distributed to multiple computers capable of communicating with each other can be implemented. For example, an embodiment in which some or all of the components of the information processing apparatus 30 are provided in the health checkup vehicle 10 can also be implemented.

As a variation, the controller 31 of the information processing apparatus 30 may provide an automated driving bus or the like to the patients to whom the transportation means other than the vehicles 20 is suggested in step S5 described above, based on a driving schedule and route set in any method by the information processing apparatus 30.

As a variation, an embodiment in which a general purpose computer functions as the information processing apparatus 30 according to the above embodiment can also be implemented. Specifically, a program in which processes for realizing the functions of the information processing apparatus 30 according to the above embodiment are written may be stored in a memory of a general purpose computer, and the program may be read and executed by a processor. Accordingly, the present disclosure can also be implemented as a program executable by a processor, or a non-transitory computer readable medium storing the program.

A part of the present embodiment will be exemplarily described below. However, it should be noted that the embodiment of the present disclosure is not limited to these.

[Appendix 1]

An information processing apparatus comprising a controller configured to:
  determine a stop location for a health checkup vehicle at which travel distances required for patients of health checkups to be performed on the health checkup vehicle to travel to the health checkup vehicle are equal to or less than a predetermined threshold;
  calculate a parking allowable number at the stop location or a parking allowable number at a parking lot in a vicinity of the stop location; and
  suggest, in a case in which the patients include more patients who plan to travel using vehicles than the parking allowable number, transportation means other than the vehicles to the patients who plan to travel using the vehicles.

[Appendix 2]

The information processing apparatus according to Appendix 1, wherein the controller is configured to identify, based on location information on homes of the patients, a patient to whom a transportation means other than a vehicle is suggested, from among the patients who plan to travel using the vehicles.

[Appendix 3]

The information processing apparatus according to Appendix 1 or 2, wherein the controller is configured to calculate the parking allowable number based on specifications of vehicles owned by the patients.

[Appendix 4]

The information processing apparatus according to any one of Appendices 1 to 3, wherein the controller is configured to suggest public transportation as the transportation means.

[Appendix 5]

A method performed by an information processing apparatus, the method comprising:
  determining a stop location for a health checkup vehicle at which travel distances required for patients of health checkups to be performed on the health checkup vehicle to travel to the health checkup vehicle are equal to or less than a predetermined threshold;
  calculating a parking allowable number at the stop location or a parking allowable number at a parking lot in a vicinity of the stop location; and suggesting, in a case in which the patients include more patients who plan to travel using vehicles than the parking allowable number, transportation means other than the vehicles to the patients who plan to travel using the vehicles.

[Appendix 6]

The method according to Appendix 5, further comprising identifying, based on location information on homes of the patients, a patient to whom transportation means other than a vehicle is suggested, from among the patients who plan to travel using the vehicles.

[Appendix 7]

The method according to Appendix 5 or 6, further comprising calculating the parking allowable number based on specifications of vehicles owned by the patients.

[Appendix 8]

The method according to any one of Appendices 5 to 7, further comprising suggesting public transportation as the transportation means.

[Appendix 9]

A program configured to cause a computer to execute operations, the operations comprising:
 determining a stop location for a health checkup vehicle at which travel distances required for patients of health checkups to be performed on the health checkup vehicle to travel to the health checkup vehicle are equal to or less than a predetermined threshold;
 calculating a parking allowable number at the stop location or a parking allowable number at a parking lot in a vicinity of the stop location; and
 suggesting, in a case in which the patients include more patients who plan to travel using vehicles than the parking allowable number, transportation means other than the vehicles to the patients who plan to travel using the vehicles.

[Appendix 10]

The program according to Appendix 9, wherein the operations further comprise identifying, based on location information on homes of the patients, a patient to whom a transportation means other than a vehicle is suggested, from among the patients who plan to travel using the vehicles.

[Appendix 11]

The program according to Appendix 9 or 10, wherein the operations further comprise calculating the parking allowable number based on specifications of vehicles owned by the patients.

[Appendix 12]

The program according to any one of Appendices 9 to 11, wherein the operations further comprise suggesting public transportation as the transportation means.

The invention claimed is:

1. An information processing apparatus comprising a controller configured to:
 determine a stop location for a health checkup vehicle at which travel distances required for patients of health checkups to be performed on the health checkup vehicle to travel to the health checkup vehicle are equal to or less than a predetermined threshold;
 calculate a parking allowable number at the stop location or a parking allowable number at a parking lot in a vicinity of the stop location;
 suggest, in a case in which the patients include more patients who plan to travel using vehicles than the parking allowable number, an automated transportation means other than the vehicles to the patients who plan to travel using the vehicles;
 generate a driving schedule and route of the automated transportation means for the patients to whom the automated transportation means is suggested; and
 control the automated transportation means to travel based on the driving schedule and route.

2. The information processing apparatus according to claim 1, wherein the controller is configured to identify, based on location information on homes of the patients, a patient to whom the automated transportation means is suggested, from among the patients who plan to travel using the vehicles.

3. The information processing apparatus according to claim 1, wherein the controller is configured to calculate the parking allowable number based on specifications of vehicles owned by the patients.

4. The information processing apparatus according to claim 1, wherein the controller is configured to suggest automated public transportation as the automated transportation means.

5. The information processing apparatus according to claim 1, wherein the controller is configured to determine a location at which a sum of the travel distances of all the patients is minimized from among a plurality of candidate locations, as the stop location for the health checkup vehicle, based on location information on homes of the patients and location information on the plurality of candidate locations.

6. A method performed by an information processing apparatus, the method comprising:
 determining a stop location for a health checkup vehicle at which travel distances required for patients of health checkups to be performed on the health checkup vehicle to travel to the health checkup vehicle are equal to or less than a predetermined threshold;
 calculating a parking allowable number at the stop location or a parking allowable number at a parking lot in a vicinity of the stop location;
 suggesting, in a case in which the patients include more patients who plan to travel using vehicles than the parking allowable number, an automated transportation means other than the vehicles to the patients who plan to travel using the vehicles;
 generating a driving schedule and route of the automated transportation means for the patients to whom the automated transportation means is suggested; and
 controlling the automated transportation means to travel based on the driving schedule and route.

7. The method according to claim 6, further comprising identifying, based on location information on homes of the patients, a patient to whom the automated transportation means is suggested, from among the patients who plan to travel using the vehicles.

8. The method according to claim 6, further comprising calculating the parking allowable number based on specifications of vehicles owned by the patients.

9. The method according to claim 6, further comprising suggesting automated public transportation as the automated transportation means.

10. The method according to claim 6, wherein determining the stop location for the health checkup vehicle comprises determining a location at which a sum of the travel distances of all the patients is minimized from among a plurality of candidate locations, as the stop location for the health checkup vehicle, based on location information on homes of the patients and location information on the plurality of candidate locations.

11. A non-transitory computer readable medium storing a program configured to cause a computer to execute operations, the operations comprising:
- determining a stop location for a health checkup vehicle at which travel distances required for patients of health checkups to be performed on the health checkup vehicle to travel to the health checkup vehicle are equal to or less than a predetermined threshold;
- calculating a parking allowable number at the stop location or a parking allowable number at a parking lot in a vicinity of the stop location;
- suggesting, in a case in which the patients include more patients who plan to travel using vehicles than the parking allowable number, an automated transportation means other than the vehicles to the patients who plan to travel using the vehicles;
- generating a driving schedule and route of the automated transportation means for the patients to whom the automated transportation means is suggested; and
- controlling the automated transportation means to travel based on the driving schedule and route.

12. The non-transitory computer readable medium according to claim 11, wherein the operations further comprise identifying, based on location information on homes of the patients, a patient to whom the automated transportation means is suggested, from among the patients who plan to travel using the vehicles.

13. The non-transitory computer readable medium according to claim 11, wherein the operations further comprise calculating the parking allowable number based on specifications of vehicles owned by the patients.

14. The non-transitory computer readable medium according to claim 11, wherein the operations further comprise suggesting automated public transportation as the automated transportation means.

15. The non-transitory computer readable medium according to claim 11, wherein determining the stop location for the health checkup vehicle comprises determining a location at which a sum of the travel distances of all the patients is minimized from among a plurality of candidate locations, as the stop location for the health checkup vehicle, based on location information on homes of the patients and location information on the plurality of candidate locations.

* * * * *